United States Patent
Schütz

(10) Patent No.: US 6,541,974 B1
(45) Date of Patent: Apr. 1, 2003

(54) DEVICE FOR STORING A GASEOUS MEDIUM IN A STORAGE CONTAINER

(75) Inventor: Walter Schütz, Weidenberg (DE)

(73) Assignee: Mannesmann AG, Düsseldorf (DE)

(*) Notice: Subject to any disclaimer, the term of this patent is extended or adjusted under 35 U.S.C. 154(b) by 0 days.

(21) Appl. No.: 09/763,300
(22) PCT Filed: Aug. 6, 1999
(86) PCT No.: PCT/DE99/02503
  § 371 (c)(1),
  (2), (4) Date: Feb. 20, 2001
(87) PCT Pub. No.: WO00/11438
  PCT Pub. Date: Mar. 2, 2000

(30) Foreign Application Priority Data

Aug. 19, 1998 (DE) .......................... 198 38 664

(51) Int. Cl.⁷ ................................. G01V 3/00
(52) U.S. Cl. ........................ 324/321; 324/300
(58) Field of Search ............... 324/300, 318, 324/322, 321, 319, 303, 306, 307, 309

(56) References Cited

U.S. PATENT DOCUMENTS 4,785,245 A  * 11/1988  Lew et al. ................. 324/307
6,166,542 A  * 12/2000  Gallop et al. .............. 324/300
6,333,629 B1 * 12/2001  Pykett et al. .............. 324/300

* cited by examiner

Primary Examiner—Louis Arana
(74) Attorney, Agent, or Firm—Cohen, Pontani, Lieberman & Pavane

(57) ABSTRACT

A device for measuring the filling level of a medium—for example hydrogen—in a storage container of a storage device—for example a tank system. To provide a simple and direct possible way of accurately determining the filling level of the storage container even without knowing the amount of medium already discharged or irrespective of uncontrollable losses, the device is designed as a measuring device for measuring the nuclear magnetic resonance of the medium located in the storage container. For this purpose, the device has a measuring head with, for example, a permanent magnet and a measuring coil, via which a static magnetic field and an electromagnetic alternating field are generated in the measuring head. The electromagnetic alternating field is generated in a transmitter, which is connected to the measuring head by a bridge circuit. The values of the nuclear magnetic resonance of the stored medium measured by the measuring head are processed via the bridge circuit and an amplifier and displayed on a display device. A corresponding storage device and a suitable measuring method are also described.

28 Claims, 1 Drawing Sheet

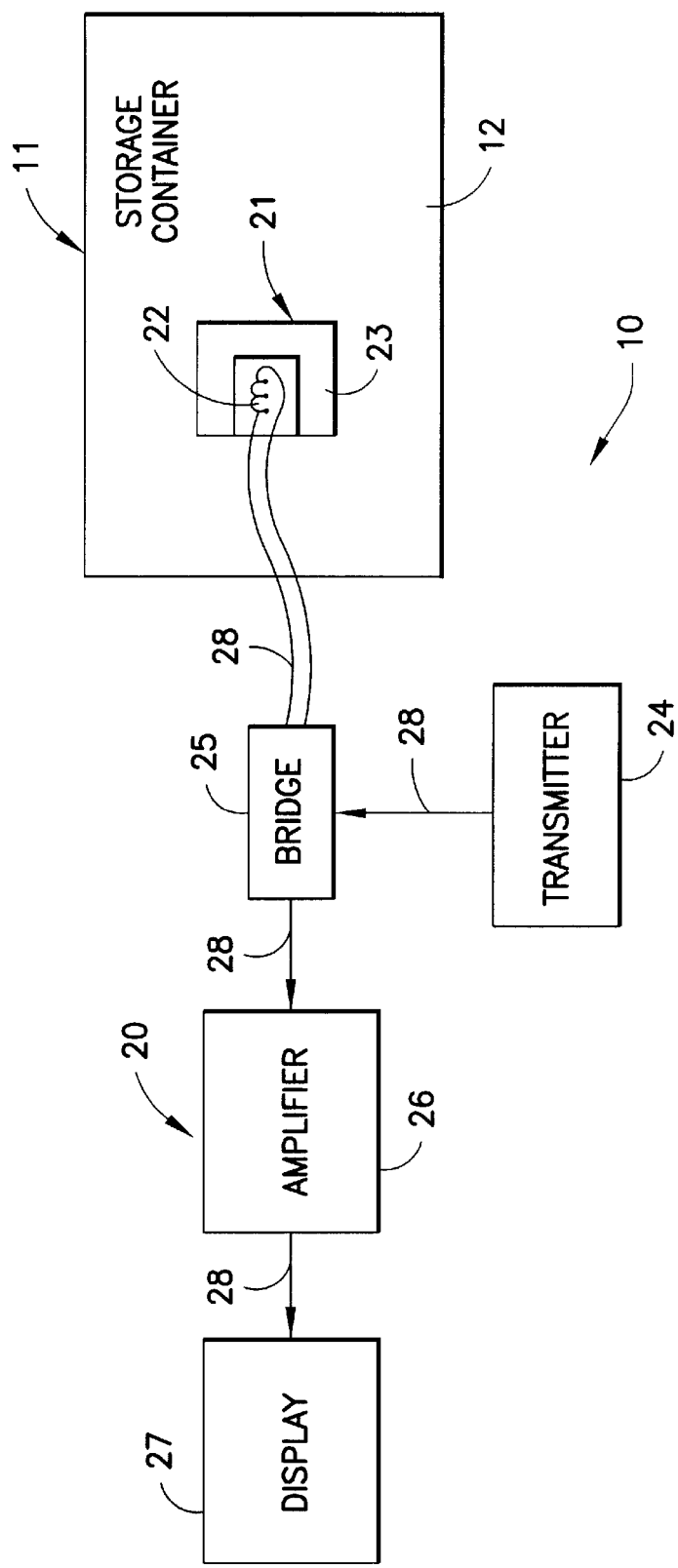

DEVICE FOR STORING A GASEOUS MEDIUM IN A STORAGE CONTAINER

PRIORITY CLAIM

This is a U.S. national stage of application No. PCT/DE99/02503, filed on Aug. 6, 1999. Priority is claimed on that application and on the following application:
Country: Germany, Application No.: 198 38 664.8, Filed: Aug. 19, 1998.

The present invention relates to a device for storing gaseous media, with a storage container for receiving the medium to be stored and a measuring device for measuring the nuclear magnetic resonance, according to the preamble of patent claim 1. Furthermore, the invention also relates to a method of measuring the filling level of a medium in a storage container.

In the storage of gaseous media in corresponding storage containers, for example in the storage of gaseous fuels such as hydrogen or natural gas in tank systems suitable for this purpose, the determination of the filling level, i.e. the stored amount of gaseous medium, in the storage container represents a major problem.

Until now, the filling level has generally been determined indirectly by the discharged amount of the gaseous medium. However, this measuring method has a series of disadvantages. For instance, firstly, a precise knowledge of the amount of the gaseous medium initially stored is required. Furthermore, possible losses, which may arise for example due to leaks in the storage container, cannot be taken into account by the known measuring method, so that inaccuracies can occur here. Due to the fact that, in the case of the known indirect measuring method, the exact filling data are required to allow indications concerning the filling level of the gaseous medium in the storage container to be given, this measuring method is not very suitable, particularly in the case of tank systems for storing gaseous fuels.

A further possible way of measuring the filling level of a gaseous medium in a storage container is to measure the pressure prevailing in the storage container. The pressure prevailing in the storage container provides information on the amount of stored gaseous medium indirectly in a manner dependent on the prevailing temperature. This measuring method can only be used, however, whenever the gaseous media are stored in the storage container with an increased pressure and there is a direct proportionality between the pressure and the amount stored.

WO 97/19 363 discloses a measuring device for determining the filling level of a gas pressure vessel which can be used in particular for space travel. This measuring device is based on the principle of nuclear magnetic resonance and has a means for generating an essentially uniform magnetic field along an axis of the gas pressure vessel and a means for generating an oscillating magnetic field transversely to the uniform magnetic field. The means for generating the two magnetic fields are formed in each case as electric windings which surround the gas pressure vessel on the outside. Such a construction requires respectively adapted electric windings for each form of container.

It is also known from U.S. Pat. No. 5,539,309 to use the principle of nuclear magnetic resonance to ascertain chemical or physical properties of samples. For this purpose, sample containers with solid or liquid content are introduced into an investigation area which lies in a static magnetic field. To generate the nuclear magnetic resonance, the sample is surrounded by an electrical winding, which generates a magnetic alternating field perpendicularly to the static magnetic field. The problem of filling level measurement of gas pressure vessels is not mentioned in this document.

SUMMARY OF INVENTION

Starting from the cited prior art, the present invention is based on the object of providing a device for storing a gaseous medium in a storage container so that the disadvantages mentioned are avoided. In particular it is intended to provide a device with as high a storage capacity as possible, in which the filling level of the gaseous medium can be determined directly in a simple, exact and uncomplicated way, without information on the history of the filling and removing operations being required and without uncontrolled losses due to leaks or the like falsifying the measurement result. Furthermore, a method of measuring the filling level of a gaseous medium in a storage container is to be provided.

The object is achieved according to the first aspect of the invention by a device for storing a gaseous medium, with a storage container for receiving the gaseous medium and with a measuring device for measuring the nuclear magnetic resonance of the gaseous medium located in the storage container. The measuring device generates a static magnetic field and an electromagnetic alternating field, the field lines of which are perpendicular to the field lines of the static magnetic field. This device is characterized in that the storage container is filled with a storage mass for storing the gaseous medium. The measuring device has a measuring head in which the static magnetic field and the electromagnetic alternating field are generated. Furthermore, the measuring head is arranged so that it covers a partial volume of the storage container, the partial volume being representative of the entire storage container with regard to the filling with the storage mass and the stored gaseous medium.

This creates the possibility of being able to measure the filling level of the stored medium directly. Apart from the type of stored medium and the temperature, no special additional knowledge is required concerning further values and data of the medium such as pressure or its filling history. The measuring principle is fundamentally suitable for all media that have atoms of which the nuclei have a magnetic moment, that is in particular hydrogen.

The basic idea of the present invention is that, for determining the filling level, the nuclear magnetic resonance (NMR) of the stored medium is measured. This makes use of the principle that some atomic nuclei, such as for example those of hydrogen, have a nuclear magnetic moment (nuclear spin). This is in interaction with an external magnetic field. In the case of hydrogen, which is considered here in more detail by way of example for better understanding, without however restricting the invention to hydrogen, the magnetic moment can be set by the external magnetic field in parallel or antiparallel to the applied magnetic field. The two setting possibilities are different in terms of energy, so that two different energy levels exist. These energy levels are differently populated in thermal equilibrium. That is to say, there are more nuclear spins in the lower energy level than in the upper energy level. The quantitative distribution between the two energy levels is dependent solely on the type of the respective medium and its temperature. If the filled medium is subject only to relatively small temperature fluctuations (for example +/−10° C.), it is possible, depending on the requirements for measuring accuracy, for the temperature influence to be ignored. In principle it is true that the difference in the population of the energy level is all the smaller the higher the temperature of the medium. Thus, if energy in the form of electromagnetic radiation is supplied to this system, with the amount of energy supplied corresponding to the difference between the two energy levels, nuclear spins are transferred from the lower energy level into the upper energy level. The result can be recorded and evaluated with regard to the actual filling of the storage container and transmitted.

Consequently, measurement of the nuclear magnetic resonance in a partial volume of the storage container covered by the measurement makes it possible, by means of extrapolation with regard to the total volume, to determine the filling level of the medium stored in the storage container via the actually prevailing quantity of atomic nuclei of the medium located in it. All that is needed for this purpose is appropriate calibration with respect to the storage volume existing in each case, in order that the ascertained measured values can be assigned to filling levels respectively determined in a manner dependent on the temperature level.

The fact that a storage mass, described in more detail further below, is additionally provided in the storage container allows an originally gaseous medium that is to be stored to enter into interaction with the storage mass in such a way that it loses its gaseous properties during the storage. In spite of this special feature, the filling level can be determined reliably with the aid of the measuring device provided according to the invention. It just has to be ensured that the partial volume covered by the measuring instrumentation is also representative of the total volume with regard to the storage mass.

According to the invention, the nuclear magnetic resonance of the stored medium can be determined by means of the CW method. For the purposes of the present invention, "CW" stands for "continuous wave" and means in principle that either the static magnetic field or the electromagnetic alternating field is changed continuously (e.g. frequency) during the measurement, while the other field, respectively, remains unchanged. If the energy of the electromagnetic alternating field coincides with the energy dissociation of the two nuclear spin levels, which depends on the size of the static magnetic field, energy is absorbed. The absorbed energy is proportional to the number of nuclear spins in the volume range covered by the measurement and is consequently also proportional to the filling level of the medium stored in the storage container.

In another embodiment, the nuclear magnetic resonance of the stored medium can be determined by means of the Fourier transform method. In this case, the static magnetic field remains constant. The electromagnetic alternating field is radiated as a pulse onto the stored medium. After the pulse, the stored medium "responds". This response signal is linked with the signal described in the above-mentioned CW method by means of Fourier transformation.

In a further embodiment, the nuclear magnetic resonance of the stored medium can be detected with a constant static magnetic field and a constant electromagnetic alternating field.

According to the invention, the device has a measuring head which covers a certain partial volume of the storage container which is filled in the same way with the medium as the remaining regions of the storage container. In the measuring head there is a static magnetic field and an electromagnetic alternating field, the field lines of the static magnetic field and of the electromagnetic alternating field being perpendicular to one another.

The static magnetic field sets the nuclear spins to their different energy levels. The electromagnetic alternating field, which corresponds in its size to the difference in energy between the energy levels, has the effect of transferring the nuclear spins from the lower energy level into the upper energy level. The difference in energy between the energy levels is directly proportional to the applied electromagnetic alternating field. The more nuclear spins there are within the measuring head, the more energy can be absorbed, so that the absorbed energy is also directly proportional to the number of nuclear spins.

The measuring head preferably has a measuring coil, via which the electromagnetic alternating field is coupled in or can be coupled in. For accurate measurement of the filling level of a medium stored in a storage container, in this case it is necessary for there to be a representative part of the stored medium, that is an identical composition and volumetric distribution and also temperature of the medium, in the region of the measuring coil. To increase the measuring accuracy, the device according to the invention may be equipped with a temperature measuring device, to allow the dependence of the measurement result on the temperature of the medium also to be taken into account.

With comparatively low likely fluctuations in the operating temperature, it is possible however to dispense entirely with such temperature measuring devices. The measuring device provided according to the invention is then expediently calibrated to an average operating temperature.

In a further development, the measuring head has an electromagnet, in particular a superconducting magnet, and/or a permanent magnet, via which the static magnetic field is generated or can be generated. Of course, the types of magnet mentioned can be used both individually and in combination.

In a further development, the electromagnetic alternating field has a frequency in the range from $10^3$ to $10^9$ Hz. The frequency advantageously lies in the range of radio frequency, that is in the megahertz range (MHz).

The design of the measuring head may differ, according to the use of a particular method of measuring the nuclear resonance, two of which have been described in more detail further above. Some design variants, which are of a purely exemplary nature however and are not to be understood as exclusive, are described below.

If the measuring head is used in the case of the CW method, the static magnetic field can be generated for example by a permanent magnet (for example a horseshoe magnet). In this case, the static magnetic field is kept constant. The electromagnetic alternating field is coupled into the measuring head as a variable field by a measuring coil. The changing of the variable electromagnetic alternating field takes place by changing the frequency. The measuring coil is surrounded by the permanent magnet in such a way that the respective field lines are perpendicular to one another. The measuring coil must be penetrated by a representative amount of the stored medium.

If in the case of the CW method it is intended for example to vary the static magnetic field and keep the electromagnetic alternating field constant, an electromagnet is used instead of the permanent magnet. A changing static magnetic field can be generated by means of the electromagnet, the field lines of which are in turn perpendicular to the field lines of the electromagnetic alternating field. Depending on requirements, a further magnet, for example a permanent magnet, may be used in addition to the electromagnet for building up the static magnetic field. The electromagnetic alternating field is coupled in at a constant frequency via a measuring coil. In turn, in the filling level measurement, the measuring coil must be penetrated by a representative amount of the stored medium.

If the measuring head is to be used in the case of the Fourier transform method, it may, for example, be designed like the variant described above for the CW method with a constant static magnetic field.

In a further development, a transmitter (frequency generator) is provided for generating the electromagnetic alternating field. The transmitter is preferably a radio-frequency transmitter and serves as the radiation source for the electromagnetic alternating field.

According to the invention, a bridge circuit is also provided. The bridge circuit acts as a kind of filter, which passes the signals from the transmitter on to the measuring head, and passes the measuring signals generated by the measuring head on to the downstream evaluation units. At the same time, the bridge circuit prevents the signals that are emitted by the transmitter from being passed on directly to the evaluation units, which could lead to damage there. Furthermore, the bridge circuit makes it possible to establish, for instance by means of a zero instrument, at which frequency the nuclei of the stored medium absorb electromagnetic radiation.

According to the invention, an amplifier may also be provided. This serves, for example, the purpose of amplifying a measuring signal emitted by the measuring head in a way appropriate for further processing.

In a further development, a display device may be provided. The display device serves for the visual display of the measured values of the nuclear magnetic resonance and consequently also for the display of the filling level of the medium stored in the storage container. It may be designed for example—but not exclusively—in the form of a recorder, scale, screen, computer or the like.

By the measuring device provided according to the invention, a measured value that is representative of the energy absorption as a result of nuclear magnetic resonance is determined and evaluated as a parameter. The higher the measured value, the higher the filling level of the medium stored in the storage container. By appropriate calibration, individual measured values can be assigned specific filling levels in relation to the storage container in question for the stored medium. However, other parameters may also be used for the evaluation, for example the relaxation times, which can change in a manner dependent on the charging of the storage container with a medium, that is to say in a manner proportional to its filling level. To be regarded as the relaxation time is the time period which elapses from when the electromagnetic alternating field is switched off until the original distribution of the nuclear spins between the energy levels is resumed, or the phase coherence of the nuclear spins among one another that was achieved by the irradiation of the electromagnetic alternating field is lost.

According to the invention, a storage mass for storing the gaseous medium, for example by adsorption, absorption or chemisorption, is provided in the storage container. The storage mass serves for increasing the storage capacity for the medium in the storage container. Use of a storage mass is therefore advantageous in particular whenever the storage device is to be used as a tank system for mobile applications. In principle, any material that is desired and suitable in a particular case, depending on requirements, the application concerned and the medium to be stored, can be used as a storage mass.

A storage mass which is particularly. suitable for the storage of hydrogen is described below by way of example.

This is because the storage of hydrogen has gained rapidly in significance in recent years. For example, hydrogen is a possible fuel for mobile applications, for instance as a fuel for electric vehicles operated on fuel cells to generate power.

Preferably, the storage mass can be formed from carbon nanostructures. Proposals have already been made to use such carbon nanostructures which have chemisorption properties for the storage of gases, and here in particular of hydrogen. Such a proposal is disclosed in WO 97/26082, the disclosure of which to this extent is incorporated by reference into the description of the present invention. The carbon nanostructures may, for example, take the form of nanofibers, nanotubes or nanoshells.

According to the invention, the carbon nanostructures may have and/or form an unoriented or oriented structure, an oriented structure being preferred.

The carbon nanostructures may advantageously be combined to form larger coherent conglomerates. Such conglomerates may, for example, have the form of pellets, platelets, tablets or the like. In this way, the storage container can be filled with the storage mass for the medium to be stored easily and with the greatest possible utilization of space.

In an advantageous development, the storage mass is therefore made up of a number of individual coherent conglomerates.

According to the invention, at least some of the conglomerates may be compacted with an apparent density that is increased in comparison with the apparent density of the originally loose carbon nanostructures. In this way, a large amount of the gaseous medium can be stored with a comparatively small storage volume of the storage container, since more storage mass is introduced into the given storage volume of the storage container than would be possible by simply filling with storage mass. In this case, apparent density is understood as meaning the weight related to the volume of the conglomerate. A storage mass as described above comprising conglomerates of carbon nanostructures is disclosed for example by DE-197 455 49.2, which was filed by the applicant and the disclosure of which is incorporated by reference into the description of the present invention.

The measuring head is advantageously arranged inside the storage container. At the same time, in principle, a specific arrangement within the storage container containing a gas is not especially important. All that is important is that a representative amount of the stored medium is located in the measuring head, in order that an exact indication of the filling level can be given. Since the stored gaseous medium is distributed equally in the storage container as it is increasingly emptied, the existing amount of stored medium measured at a certain point in the storage container is representative of the total amount of the medium stored in the storage container—unlike in the case of purely liquid-containing containers. Consequently, an exact indication of the filling level of the medium stored in the storage container can be obtained even with a relatively small measuring head.

In some cases it is advantageous to install the measuring head not directly in the storage container but in a space which, for example, is formed as a measuring tube which is closed at one end and flow-connected directly to the interior of the storage container, so that identical measuring conditions with respect to the stored medium as in the storage container prevail in said measuring tube. Therefore, according to the invention, the measuring head must also be penetrated by the storage mass, i.e. it must be embedded in the storage mass.

In a preferred development, the medium to be stored is hydrogen.

The fact that the medium is stored in a storage mass makes the advantages of the present invention become particularly clear. As the following example shows, this is so because, apart from the method of filling level determination by weight measurements, which is often not feasible for mobile applications, satisfactory determination of the filling level cannot be obtained by conventional methods (for example by pressure measurement). If, for example, a pressure vessel is filled with carbon nanofibers as the storage medium, different charging and discharging characteristics are obtained for instance for hydrogen than in the case of a customary compressed hydrogen store. After charging with hydrogen at pressures above, for example, 100 bar, part of the hydrogen is chemisorbed in the storage medium. During discharging, below a certain pressure level the hydrogen is released again from the fibers. This means that, until this lower pressure level is reached, the removal of hydrogen takes place essentially from the interstices between the fibers. Only when the pressure falls further does desorption of the hydrogen commence, so that the outflow of the hydrogen from the interstices of the carbon nanofibers is largely compensated by the desorbed hydrogen, that is to say the pressure remains constant. The actual filling with hydrogen is therefore much higher than would in fact correspond to the pressure respectively measured (in the case of a pressure vessel without storage mass). A measurement by the device according to the invention, on the other hand, can ascertain not only the amount of hydrogen stored in the interstices but also the amount of hydrogen chemisorbed in the storage mass.

According to a second aspect of the present invention, a method of measuring the filling level of a medium in a storage device according to the invention is provided and is characterized by the following steps: a) generating a static magnetic field and an electromagnetic alternating field in the measuring head, which is arranged in the storage container or in a measuring tube flow-connected to the storage container; b) measuring the nuclear magnetic resonance of the stored medium by means of the measuring head, the measuring head being penetrated by a representative amount of the storage mass and of the stored medium; and c) displaying on a display device a result corresponding to the filling level on the basis of the measured values.

The method according to the invention allows a direct determination of the filling level of the medium stored in the storage container to be performed in a simple way, without the disadvantages mentioned in the introductory part of the description occurring. For the advantages, results, effects and functional mode of the method according to the invention, reference is made fully to the comments made above concerning the storage device according to the invention.

In a further development, the measured values of the nuclear magnetic resonance of the stored medium may be preprocessed and/or further processed before display on the display device. This can take place for example with the aid of a computer.

BRIEF DESCRIPTION OF THE DRAWINGS

The invention is now explained in more detail on the basis of an exemplary embodiment with reference to the attached drawing, in which the single FIGURE shows the schematic design of a storage device according to the invention.

DETAILED DESCRIPTION OF THE PREFERRED EMBODIMENTS

The storage device 10 has, firstly, a storage container 11, in which hydrogen is stored. To increase the storage capacity, inside the storage container 11 there is a storage mass 12. The storage mass 12 comprises a number of conglomerates, which are formed from carbon nanofibers.

The storage device 10 also has a device 20 for measuring the filling level of the hydrogen stored in the storage container 11. The measuring device 20 is designed in such a way that it can measure the nuclear magnetic resonance of the hydrogen. The measuring device 20 has a measuring head 21, which is formed by a permanent magnet 23 and a measuring coil 22. The permanent magnet 23 is a horseshoe magnet, which encloses the measuring coil 22. It serves for generating a constant static magnetic field. An electromagnetic alternating field at radio frequency is coupled in by means of the measuring coil 22, with the field lines of the static magnetic field and of the electromagnetic alternating field being perpendicular to one another.

The electromagnetic alternating field is generated in a transmitter 24, which is connected to the measuring coil 22 of the measuring head 21 via a bridge circuit 25 and corresponding lines 28.

The bridge circuit 25 passes the nuclear magnetic resonance values measured by the measuring head 21, which were ascertained in the way described further above, via an amplifier 26 into a display device 27, which in the present case is designed as a pointer instrument. For this purpose, the individual elements are in turn connected to one another by means of lines 28. Furthermore, the bridge circuit 25 prevents signals from the transmitter 24 from being passed on directly to the amplifier 26, which could cause damage in this device.

Alternatively, the individual units which have been described above may also be designed as an integrated circuit or be produced and assembled by means of microsystem technology.

The functional mode of the measuring device 20 is now described below.

The filling level of hydrogen in a tank system which has a storage container 11 filled with carbon nanofibers as the storage mass 12 is to be measured by the measuring device 20. For this purpose, firstly a constant static magnetic field is generated by means of the permanent magnet 23 of the measuring head 21. The static magnetic field sets the nuclear spins of the hydrogen in parallel or antiparallel to the applied static magnetic field, whereby two different energy levels with a certain difference in energy are produced. To allow an accurate indication of the filling level of the hydrogen to be given, the measuring head must be penetrated by an amount of the hydrogen and also of the storage mass 12 that is representative of the entire storage container 11.

A variable electromagnetic alternating field at radio frequency, which was generated in advance in the transmitter 24, is coupled into the measuring head 21 by means of the measuring coil 22. The variation of the electromagnetic alternating field takes place by changing the frequency. The measuring coil 22 and the permanent magnet 23 must be aligned in relation to each other in such a way that the field lines of the static magnetic field and of the electromagnetic alternating field are perpendicular to one another.

Supplying the electromagnetic alternating field has the effect that nuclear spins of the hydrogen are transferred from the lower energy level into the upper energy level, whereby the energy of the electromagnetic alternating field is absorbed. The more nuclear spins there are within the measuring coil 22, the more energy can be absorbed. The absorbed energy is consequently directly proportional to the number of nuclear spins. For the tank system mentioned, this means that the absorbed energy is always directly proportional to the filling level of the storage container 11 if there is a representative part of the storage mass and of the stored hydrogen within the measuring coil 21.

The values of the nuclear magnetic resonance of the hydrogen measured by the measuring head 21, or the values for the absorbed energy, are passed on via the bridge circuit 25 and the amplifier 26 to the display device 27, designed as a pointer instrument.

Depending on requirements, the measured values may also be preprocessed and further processed in a further suitable device (not represented), for example a computer or the like, before they are output to the pointer instrument 27.

It is to be seen as a great advantage of the storage device according to the invention that the measuring head for carrying out the measurement of the nuclear magnetic resonance is completely independent of the shape and size of the respective storage container. Consequently, low-cost and quality-assured mass production of this component is possible.

Accommodating the measuring head in the storage container ensures that the measuring head is very well protected from being damaged.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A device for storing a gaseous medium, comprising: a storage container for receiving the gaseous medium, the storage container being filled with a storage mass for storing the gaseous medium; and means for measuring nuclear magnetic resonance of the gaseous medium located in the storage container, the measuring means being operative to generate a static magnetic field with field lines and an electromagnetic alternating field with field lines that are perpendicular to the field lines of the static magnetic field, the measuring means including a measuring head in which the static magnetic field and the electromagnetic alternating field are generated, the measuring head being arranged inside the storage container so that the measuring head covers a partial volume, the partial volume being representative of the entire storage container with regard to filling with the storage mass and the stored gaseous medium.

2. A device as defined in claim 1, wherein the measuring means is operative for measuring the nuclear magnetic resonance of the stored medium by a continuous wave (CW) method.

3. A device as defined in claim 1, wherein the measuring means is operative for determining the nuclear magnetic resonance of the stored medium by a Fourier transform method.

4. A device as defined in claim 1, wherein the measuring means is operative for determining the nuclear magnetic resonance of the stored medium with a constant static magnetic field and a constant electromagnetic alternating field.

5. A device as defined in claim 1, wherein the measuring head has a measuring coil whereby the electromagnetic alternating field is coupleable via the measuring coil.

6. A device as defined in claim 1, wherein the measuring head has at least one of an electromagnet and a permanent magnet via which the static magnetic field is generateable.

7. A device as defined in claim 6, wherein the measuring head has a super conducting magnet.

8. A device as defined in claim 1, wherein the electromagnetic alternating field has a frequency in a range of $10^3$ to $10^9$ Hz.

9. A device as defined in claim 8, wherein the electromagnetic alternating field has a frequency in the range of radio frequency.

10. A device as defined in claim 1, and further comprising a transmitter operative to generate the electromagnetic alternating field.

11. A device as defined in claim 10, and further comprising a display device connected to the measuring means.

12. A device as defined in claim 11, and further comprising an amplifier connected to the display device.

13. A device as defined in claim 12, and further comprising a bridge circuit arranged so as to couple the measuring head, the transmitter and the display device to one another.

14. A device as defined in claim 1, and further comprising means for recording temperature of the medium.

15. A device as defined in claim 1, wherein the storage mass is formed by carbon nanostructures.

16. A device as defined in claim 15, wherein the carbon nanostructures have an oriented structure.

17. A device as defined in claim 15, wherein the carbon nanostructures have and form an oriented structure.

18. A device as defined in claim 15, wherein the carbon nanostructures are one of nanofibers, nanotubes and nanoshells.

19. A device as defined in claim 15, wherein the carbon nanostructures form an oriented structure.

20. A device as defined in claim 15, wherein the carbon nanostructures are combined to form larger coherent conglomerates.

21. A device as defined in claim 20, wherein at least individual conglomerates are compacted with an apparent density that is increased in comparison with apparent density of originally loose carbon nanostructures.

22. A device as defined in claim 1, wherein the storage mass is made up of a number of individual coherent conglomerates.

23. A device as defined in claim 22, wherein at least individual conglomerates are compacted with an apparent density that is increased in comparison with apparent density of originally loose carbon nanostructures.

24. A device as defined in claim 1, wherein the gaseous medium is hydrogen.

25. A method of measuring a filling level of a gaseous medium stored in a storage mass in a storage container, comprising the steps of:
  a) generating a static magnetic field and an electromagnetic alternating field in a measuring head which is arranged in the storage container;
  b) measuring nuclear magnetic resonance of the stored medium with the measuring head, the measuring head being penetrated by a representative amount of the storage mass and of the stored gaseous medium;
  c) displaying on a display device a result corresponding to the filling level based on the measured values.

26. A method as defined in claim 25, wherein the measured values of nuclear magnetic resonance of the stored medium are at least one of preprocessed and further processed before display on the display device.

27. A device for storing a gaseous medium, comprising: a storage container for receiving the gaseous medium, the storage container being filled with a storage mass for storing the gaseous medium; and means for measuring nuclear magnetic resonance of the gaseous medium located in the storage container, the measuring means being operative to generate a static magnetic field with field lines and an electromagnetic alternating field with field lines that are perpendicular to the field lines of the static magnetic field, the measuring means including a measuring head in which the static magnetic field and the electromagnetic alternating field are generated, the measuring head being arranged in a measuring tube in fluid communication with the storage container so that the measuring head covers a partial volume, the partial volume being representative of the entire storage container with regard to filling with the storage mass and the stored gaseous medium.

28. A method of measuring a filling level of a gaseous medium stored in a storage mass in a storage container, comprising the steps of:
   a) generating a static magnetic field and an electromagnetic alternating field in a measuring tube in fluid communication with the storage container;
   b) measuring nuclear magnetic resonance of the stored medium with the measuring head, the measuring head being penetrated by a representative amount of the storage mass and of the stored gaseous medium;
   c) displaying on a display device a result corresponding to the filling level based on the measured values.

* * * * *